(12) United States Patent
Grey et al.

(10) Patent No.: US 8,409,088 B2
(45) Date of Patent: Apr. 2, 2013

(54) RETRACTOR ILLUMINATION SYSTEM

(75) Inventors: Thomas Grey, San Marco, CA (US);
Alex Vayser, Mission Viejo, CA (US);
Jon Gasson, San Francisco, CA (US)

(73) Assignee: Invuity, Inc., San Francisco, CA (US)

( * ) Notice: Subject to any disclaimer, the term of this patent is extended or adjusted under 35 U.S.C. 154(b) by 839 days.

(21) Appl. No.: 11/654,874

(22) Filed: Jan. 17, 2007

(65) Prior Publication Data

US 2007/0208226 A1 Sep. 6, 2007

Related U.S. Application Data

(60) Provisional application No. 60/760,167, filed on Jan. 18, 2006.

(51) Int. Cl.
*A61B 17/08* (2006.01)
*A61M 29/00* (2006.01)

(52) U.S. Cl. .................................... 600/212; 600/191

(58) Field of Classification Search ........... 600/200–249
See application file for complete search history.

(56) References Cited

U.S. PATENT DOCUMENTS

| | | | |
|---|---|---|---|
| 1,246,339 A | 11/1917 | Smit | |
| 1,326,300 A | 12/1919 | Smit | |
| 2,186,143 A | 1/1940 | Neugass | 128/16 |
| 2,235,979 A | 3/1941 | Brown | 128/6 |
| 2,247,258 A | 6/1941 | Shepard | 128/16 |
| 2,482,971 A | 9/1949 | Golson | 128/6 |
| 3,075,516 A | 1/1963 | Strauch | 128/6 |
| 3,261,350 A | 7/1966 | Wallace | 128/6 |
| 3,328,570 A | 6/1967 | Balchunas | 240/2.1 |
| 3,590,232 A | 6/1971 | Sadowski | 240/2 |
| 3,638,644 A | 2/1972 | Reick | |
| 3,641,332 A | 2/1972 | Reick et al. | |
| 3,664,330 A | 5/1972 | Deutsch | 128/18 |
| 3,680,546 A | 8/1972 | Asrican | 128/18 |
| 3,712,705 A | 1/1973 | Marcatili | 350/96 |
| 3,807,393 A | 4/1974 | McDonald | 128/20 |

(Continued)

FOREIGN PATENT DOCUMENTS

| | | |
|---|---|---|
| EP | 0101781 A1 | 3/1984 |
| GB | 1242374 | 8/1971 |

(Continued)

OTHER PUBLICATIONS

European search report dated Jan. 20, 2010 for EP 07718261.6.
International search report and written opinion dated Oct. 4, 2007 for PCT/US2007/001385.
U.S. Appl. No. 13/454,825, filed Apr. 24, 2012, Grey et al.

(Continued)

*Primary Examiner* — Kevin T Truong
*Assistant Examiner* — Matthew Lawson
(74) *Attorney, Agent, or Firm* — Wilson, Sonsini, Goodrich & Rosati

(57) ABSTRACT

A surgical illumination system includes a retractor having a proximal handle portion and a distal portion adapted for insertion into a surgical field and retraction of body tissue, and a light guide disposed on the retractor, said light guide having a distal surface adapted to face the surgical field when in use in retracting body tissue away from a surgical field, and a proximal aperture adapted to receive light from a light engine or other light source wherein a portion of the distal surface adapted to face the surgical field is faceted with a plurality of facets, ridges, steps or shoulders, wherein the distally oriented surface of said facets, ridges, steps or shoulders are angled relative to the axis of the light guide and the location of the surgical field such that light passing through the light guide is emitted and directed toward the surgical field.

12 Claims, 10 Drawing Sheets

U.S. PATENT DOCUMENTS

| | | | | |
|---|---|---|---|---|
| 3,829,675 A | 8/1974 | Mariani | | 240/1 |
| 3,890,960 A | 6/1975 | Wunsch, nee Kuhn et al. | | 128/16 |
| 3,892,959 A | 7/1975 | Pulles | | 240/1 |
| 3,901,674 A | 8/1975 | Strack et al. | | 65/3 |
| 3,950,073 A | 4/1976 | Horiguchi et al. | | 350/96 |
| 4,023,903 A | 5/1977 | Scheib | | 355/71 |
| 4,043,636 A | 8/1977 | Eberhardt et al. | | 350/160 |
| 4,052,980 A | 10/1977 | Grams et al. | | 128/18 |
| 4,173,392 A | 11/1979 | Ekinaka et al. | | 350/96.26 |
| 4,226,228 A | 10/1980 | Shin et al. | | 128/20 |
| 4,257,084 A | 3/1981 | Reynolds | | 362/31 |
| 4,300,541 A | 11/1981 | Burgin | | 128/18 |
| 4,306,546 A | 12/1981 | Heine et al. | | 128/6 |
| 4,337,763 A | 7/1982 | Petrassevich | | 128/20 |
| 4,471,412 A | 9/1984 | Mori | | 362/32 |
| 4,500,181 A | 2/1985 | Takahashi | | 350/574 |
| 4,562,832 A | 1/1986 | Wilder et al. | | 128/20 |
| 4,592,344 A | 6/1986 | Scheer | | |
| 4,597,030 A | 6/1986 | Brody et al. | | 362/32 |
| 4,605,990 A | 8/1986 | Wilder et al. | | |
| 4,616,635 A | 10/1986 | Caspar et al. | | 128/20 |
| 4,630,895 A | 12/1986 | Abdala, Jr. et al. | | 350/345 |
| 4,643,172 A | 2/1987 | Taff et al. | | |
| 4,686,972 A | 8/1987 | Kurland | | 128/92 |
| 4,697,578 A | 10/1987 | Burgin | | |
| 4,714,983 A | 12/1987 | Lang | | 362/27 |
| 4,733,332 A | 3/1988 | Yamashita et al. | | 362/32 |
| 4,765,701 A | 8/1988 | Cheslak | | 350/96.1 |
| 4,785,796 A | 11/1988 | Mattson | | 128/9 |
| 4,790,751 A | 12/1988 | Reinhardt et al. | | 433/29 |
| 4,790,752 A | 12/1988 | Cheslak | | 433/37 |
| 4,802,460 A | 2/1989 | Ohkuwa et al. | | 128/6 |
| 4,807,599 A | 2/1989 | Robinson et al. | | 128/16 |
| 4,842,356 A | 6/1989 | Mori | | |
| 4,885,663 A | 12/1989 | Parker | | 362/32 |
| 4,897,771 A | 1/1990 | Parker | | 362/298 |
| 4,905,082 A | 2/1990 | Nishigaki et al. | | 358/98 |
| 4,907,132 A | 3/1990 | Parker | | 362/32 |
| 4,961,617 A | 10/1990 | Shahidi et al. | | |
| 4,968,124 A | 11/1990 | Deckert et al. | | 350/574 |
| 4,974,122 A | 11/1990 | Shaw | | 362/31 |
| 5,005,108 A | 4/1991 | Pristash et al. | | 362/31 |
| 5,035,232 A | 7/1991 | Lutze et al. | | 128/20 |
| 5,039,198 A | 8/1991 | VanBeek | | 385/117 |
| 5,052,778 A | 10/1991 | Jamshid | | 385/125 |
| 5,097,396 A | 3/1992 | Myers | | 362/32 |
| 5,136,480 A | 8/1992 | Pristash et al. | | 362/31 |
| 5,159,921 A | 11/1992 | Hoover | | 128/20 |
| 5,165,387 A | 11/1992 | Woodson | | 128/6 |
| 5,207,493 A | 5/1993 | Murase et al. | | 362/31 |
| 5,209,757 A | 5/1993 | Krug et al. | | 606/162 |
| 5,226,105 A | 7/1993 | Myers | | 385/147 |
| 5,237,985 A | 8/1993 | Hodgson et al. | | 128/17 |
| 5,281,134 A | 1/1994 | Schultz | | 433/29 |
| 5,295,216 A | 3/1994 | Halter | | 385/120 |
| 5,303,323 A | 4/1994 | Mezei | | 385/147 |
| 5,307,245 A | 4/1994 | Myers et al. | | 362/32 |
| 5,312,569 A | 5/1994 | Mezei | | 264/1.5 |
| 5,312,570 A | 5/1994 | Halter | | 264/1.5 |
| 5,334,150 A | 8/1994 | Kaali | | 604/164 |
| 5,353,786 A | 10/1994 | Wilk | | 128/23 |
| 5,354,302 A | 10/1994 | Ko | | 606/104 |
| 5,377,084 A | 12/1994 | Kojima et al. | | 362/31 |
| 5,390,085 A | 2/1995 | Mari-Roca et al. | | 362/31 |
| 5,394,863 A | 3/1995 | Sanford et al. | | 128/3 |
| 5,400,773 A | 3/1995 | Zhu et al. | | 128/20 |
| 5,431,153 A | 7/1995 | Lee | | 600/183 |
| 5,432,876 A | 7/1995 | Appeldorn et al. | | 385/31 |
| 5,441,041 A | 8/1995 | Sauer et al. | | 600/106 |
| 5,445,142 A | 8/1995 | Hassler, Jr. | | 600/105 |
| 5,448,990 A | 9/1995 | De Faria-Correa | | 600/129 |
| 5,467,208 A | 11/1995 | Kokawa et al. | | 359/49 |
| 5,499,912 A | 3/1996 | Mezei | | 425/363 |
| 5,520,611 A | 5/1996 | Rao et al. | | 600/245 |
| 5,521,342 A | 5/1996 | Bartley et al. | | 200/5 |
| 5,521,797 A | 5/1996 | Kashima et al. | | 362/31 |
| 5,562,696 A | 10/1996 | Nobles et al. | | 606/185 |
| 5,571,215 A | 11/1996 | Sterman et al. | | 623/66 |
| 5,584,796 A | 12/1996 | Cohen | | 600/201 |
| 5,588,949 A | 12/1996 | Taylor et al. | | 600/166 |
| 5,588,951 A | 12/1996 | Zhu et al. | | 600/207 |
| 5,591,192 A | 1/1997 | Privitera et al. | | 606/185 |
| 5,598,280 A | 1/1997 | Nishio et al. | | 349/57 |
| 5,613,751 A | 3/1997 | Parker et al. | | 362/31 |
| 5,618,096 A | 4/1997 | Parker et al. | | 362/31 |
| 5,618,260 A * | 4/1997 | Caspar et al. | | 600/210 |
| 5,630,795 A | 5/1997 | Kuramoto et al. | | 604/30 |
| 5,759,150 A | 6/1998 | Konou et al. | | 600/114 |
| 5,775,791 A | 7/1998 | Yoshikawa et al. | | 362/31 |
| 5,779,338 A | 7/1998 | Ishikawa et al. | | 362/31 |
| 5,785,648 A | 7/1998 | Min | | 600/206 |
| 5,786,665 A | 7/1998 | Ohtsuki et al. | | 313/512 |
| 5,817,005 A | 10/1998 | Cohen | | 600/201 |
| 5,845,038 A | 12/1998 | Lundin et al. | | 385/901 |
| 5,876,107 A | 3/1999 | Parker et al. | | 362/31 |
| 5,891,013 A | 4/1999 | Thompson | | 600/104 |
| 5,895,115 A | 4/1999 | Parker et al. | | 362/511 |
| 5,913,818 A | 6/1999 | Co et al. | | 600/204 |
| 5,921,652 A | 7/1999 | Parker et al. | | 362/31 |
| 5,961,198 A | 10/1999 | Hira et al. | | 362/31 |
| 5,967,971 A | 10/1999 | Bolser | | 600/211 |
| 5,982,969 A | 11/1999 | Sugiyama et al. | | 385/123 |
| 5,995,288 A | 11/1999 | Kashima et al. | | 359/599 |
| 6,033,361 A | 3/2000 | Co et al. | | 600/210 |
| 6,079,838 A | 6/2000 | Parker et al. | | 362/31 |
| 6,129,662 A | 10/2000 | Li et al. | | 600/182 |
| 6,139,493 A * | 10/2000 | Koros et al. | | 600/215 |
| 6,176,824 B1 | 1/2001 | Davis | | 600/178 |
| 6,185,356 B1 | 2/2001 | Parker et al. | | 385/133 |
| 6,196,968 B1 | 3/2001 | Rydin et al. | | 600/210 |
| 6,210,325 B1 | 4/2001 | Bartie et al. | | 600/229 |
| 6,228,025 B1 | 5/2001 | Hipps et al. | | 600/213 |
| 6,304,712 B1 | 10/2001 | Davis | | 385/147 |
| 6,322,499 B1 | 11/2001 | Evans et al. | | 600/212 |
| 6,427,034 B1 | 7/2002 | Meis et al. | | 385/14 |
| 6,504,985 B2 | 1/2003 | Parker et al. | | 385/133 |
| 6,551,346 B2 | 4/2003 | Crossley | | 607/88 |
| 6,554,768 B1 | 4/2003 | Leonard | | 600/213 |
| 6,565,225 B2 | 5/2003 | Mabuchi et al. | | 362/31 |
| 6,805,666 B2 * | 10/2004 | Holland et al. | | 600/212 |
| 6,817,978 B2 * | 11/2004 | Holland et al. | | 600/212 |
| 6,893,394 B2 | 5/2005 | Douglas et al. | | 600/205 |
| 6,910,783 B2 | 6/2005 | Mezei et al. | | 362/31 |
| 7,223,233 B2 | 5/2007 | Branch et al. | | 600/212 |
| 7,306,559 B2 | 12/2007 | Williams | | |
| 7,311,662 B2 * | 12/2007 | Holland et al. | | 600/212 |
| 7,371,213 B2 * | 5/2008 | Hestad et al. | | 600/245 |
| 7,474,820 B2 * | 1/2009 | Vayser et al. | | 385/31 |
| 7,503,894 B2 * | 3/2009 | Vankoski et al. | | 600/245 |
| 7,510,524 B2 * | 3/2009 | Vayser et al. | | 600/178 |
| 2003/0095781 A1 * | 5/2003 | Williams | | 385/146 |
| 2003/0171408 A1 * | 9/2003 | Caplan | | 514/343 |
| 2004/0143169 A1 | 7/2004 | Branch et al. | | |
| 2004/0172105 A1 | 9/2004 | Vankoski et al. | | 607/88 |
| 2004/0236185 A1 * | 11/2004 | Holland et al. | | 600/212 |
| 2005/0159651 A1 | 7/2005 | Raymond et al. | | 600/213 |
| 2005/0165283 A1 * | 7/2005 | Hestad et al. | | 600/212 |
| 2005/0171408 A1 | 8/2005 | Parker | | |
| 2005/0182301 A1 | 8/2005 | Acker et al. | | 600/204 |
| 2005/0194876 A1 | 9/2005 | Shimada et al. | | |
| 2006/0069314 A1 | 3/2006 | Farr | | 600/179 |
| 2006/0106381 A1 * | 5/2006 | Ferree et al. | | 606/61 |
| 2006/0224045 A1 | 10/2006 | Whipple et al. | | 600/245 |
| 2006/0268570 A1 * | 11/2006 | Vayser et al. | | 362/572 |
| 2007/0066872 A1 * | 3/2007 | Morrison et al. | | 600/212 |

FOREIGN PATENT DOCUMENTS

| | | | | |
|---|---|---|---|---|
| GB | 1435600 | 5/1976 | | |
| GB | 2078526 | 1/1982 | | 17/2 |
| GB | 2133694 | * 10/1983 | | |
| GB | 2133694 | 8/1984 | | 17/2 |
| JP | 2003-162904 | 6/2003 | | |
| WO | WO96/17206 | 6/1996 | | |
| WO | WO96/37730 | 11/1996 | | |
| WO | WO00/50807 | 8/2000 | | |

| | | | |
|---|---|---|---|
| WO | WO 02/19919 A2 | 3/2002 |
| WO | WO 02/19919 A3 | 5/2002 |
| WO | WO03082123 A | 10/2003 |
| WO | WO 03/082123 A3 | 7/2004 |
| WO | WO2004077922 A | 9/2004 |
| WO | WO 2004/077922 A3 | 3/2005 |

OTHER PUBLICATIONS

European search report and opinion dated Jun. 4, 2012 for EP 12165888.4.

* cited by examiner

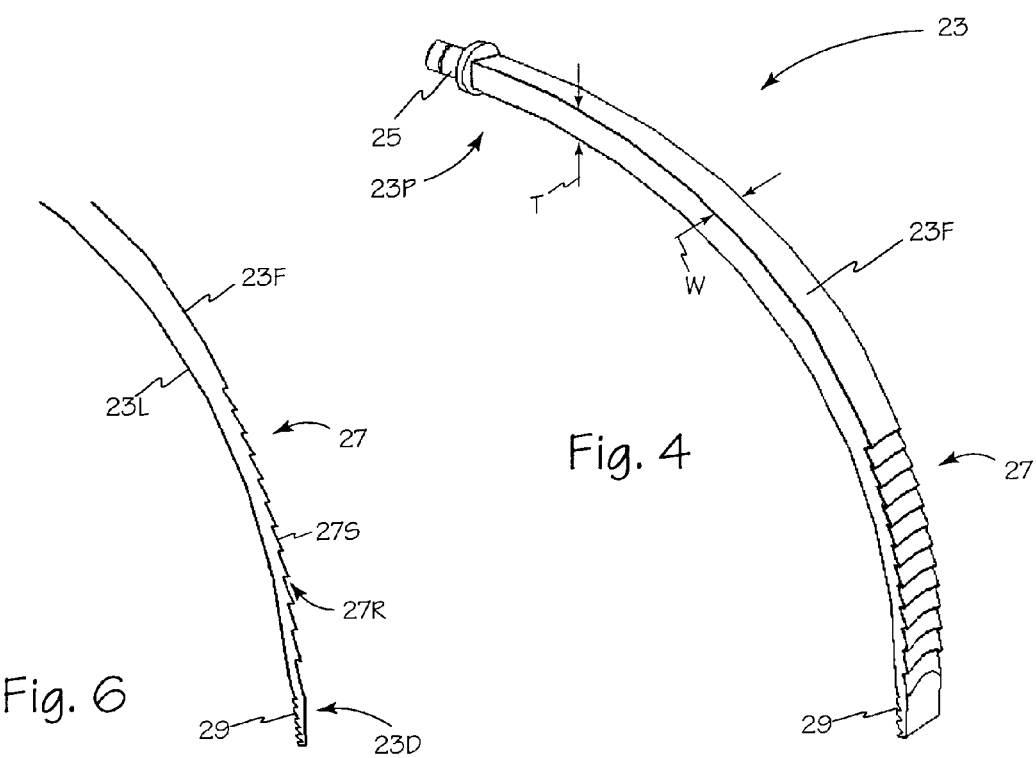
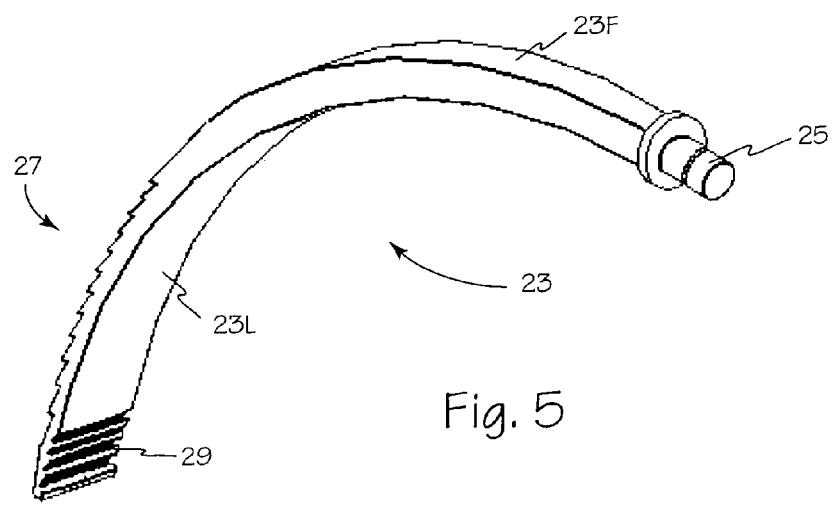

RETRACTOR ILLUMINATION SYSTEM

RELATED APPLICATIONS

This application claims priority to co-pending U.S. provisional patent application 60/760,167 filed Jan. 18, 2006.

FIELD OF THE INVENTIONS

The inventions described below relate to the field of illumination of tissue and surgical work space within the body during surgery, especially during minimally invasive surgery.

BACKGROUND OF THE INVENTIONS

Existing technology for illumination during surgical/medical procedures is generally overhead illumination. This illumination comes from either raised fixtures above the surgical field or head mounted fiber optic systems. Traditional overhead lighting systems include numerous limitations. Direct exposure of the field from the overhead source is required. Changes in patient or surgeon positioning may interfere with the illumination. Frequent adjustments are an inconvenience for the surgeon and disrupt the surgical flow. Overhead lighting is frequently inadequate for surgery in deeper cavities where more intense focused illumination may be required. In addition, the alignment of the surgeons head frequently interferes with the remote illumination and prevents light from reaching the field. Head mounted fiber optic systems are often used for more limited surgical exposures. However, these devices also have numerous limitations. First, the surgeon is tethered by the light cord attached to the headset, limiting mobility in the operating room. Second, the devices are associated with head and neck fatigue from frequent or prolonged use. Third, the devices require the surgeon to maintain a steady head and neck position to provide a constant and steady illumination of the field. Fourth, the use of remote light sources and fiber bundles introduces tremendous inefficiencies into the system. An approximate 10% loss per foot of cable is not uncommon. (for example, a 300 Watt light source and a 10 ft cable will only provide a few watts of illumination at the surgical site)

With the introduction of newer minimally invasive surgical techniques, the demand has risen for the delivery of high intensity light through minimal surgical incisions into deep surgical fields. To satisfy this need, light delivery devices have been developed for delivery of light from a remote, high intensity light source to the surgical field. The devices consist of bundles of optical fibers that directly attach to the top surface of surgical retractors to illuminate the surgical field and are connected via fiber optic cable to a high intensity light source. While these fiber-based illumination devices provide a technique for directly illuminating the surgical field, they are cumbersome and inconvenient. Due their position on top of the retractor, they get in the way and occupy valuable work space. Similar to the head mounted fiber optic systems, they provide inefficient illumination. They provide either a spot of light, which must be constantly moved around to illuminate different areas of the surgical field, or such broadly distributed light that there is insufficient illumination of the area of interest and much of that light shines back up into the surgeon's eyes.

The devices described below provide efficient illumination that may be tailored to the illumination requirements for a given surgical field.

SUMMARY

The surgical illumination system may include a retractor having a proximal handle portion and a distal portion adapted for insertion into a surgical field and retraction of body tissue, and a light guide disposed on the retractor, said light guide having a distal surface adapted to face the surgical field when in use in retracting body tissue away from a surgical field, and a proximal aperture adapted to receive light from a light engine or other light source wherein a portion of the distal surface adapted to face the surgical field is faceted with a plurality of facets, ridges, steps or shoulders, wherein the distally oriented surface of said facets, ridges, steps or shoulders are angle relative to the axis of the light guide and the location of the surgical field such that light passing through the light guide is emitted and directed toward the surgical field.

An alternate medical retractor illumination system may include a light guide retractor having a distal end, a proximal end, an upper surface and a lower surface, the lower surface is adapted to engage tissue to expose a surgical field, the light guide retractor having an input adapter and one or more light emitting surfaces to illuminate the surgical field, and a light source providing illumination energy to the input adapter.

Another medical retractor illumination system may include a retractor having a distal and a proximal end and a shape adapted to engage tissue to expose a surgical field, and a light guide conforming to the shape of the retractor and removably secured to the retractor, the light guide having an input adapter and one or more light emitting surfaces to illuminate the surgical field, and a light source providing illumination energy to the input adapter.

BRIEF DESCRIPTION OF THE DRAWINGS

FIG. 4 is a light guide with an input and light directing structures on the front and back surfaces.

FIG. 5 is a rear view of the light guide of FIG. 4 showing the rear light directing structures.

FIG. 6 is a section view of the light guide of FIG. 4 showing the stepped facets of the light directing structures.

DETAILED DESCRIPTION OF THE INVENTIONS

Figure 1:
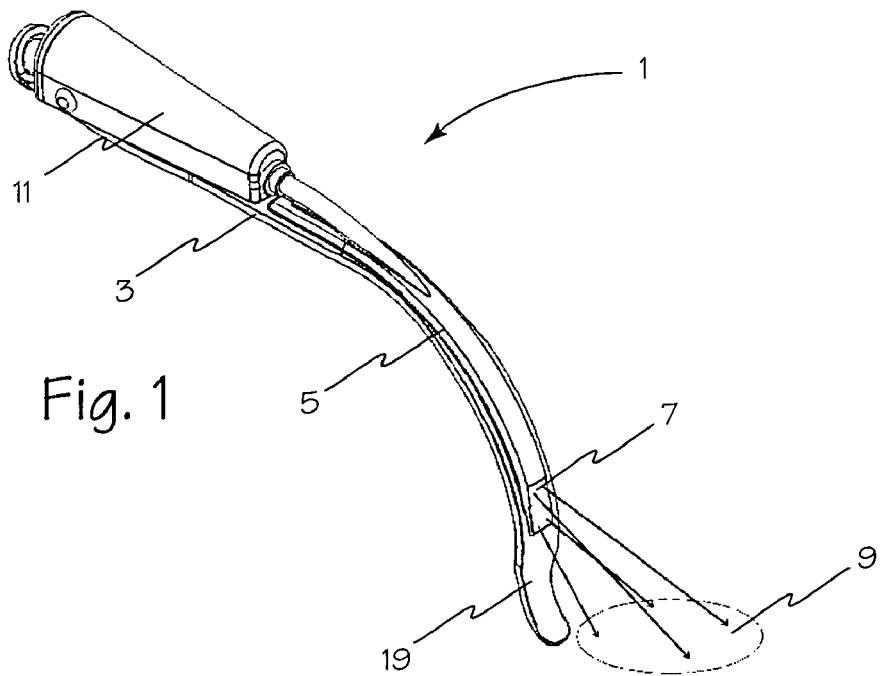
FIG. 1 is a surgical retractor blade fitted with an attachable illuminator and light source.
Figure 2:
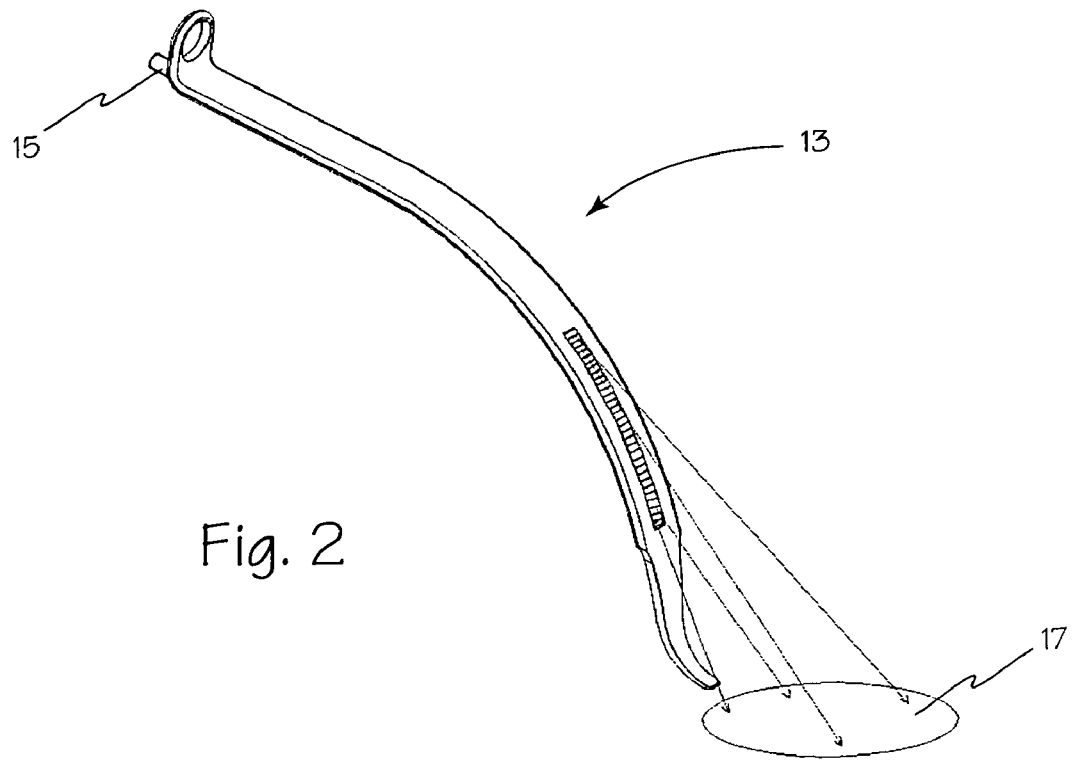
FIG. 2 is an integrated illuminating retractor wherein the light guide is shaped to match the form and function of a standard retractor.

FIGS. 1 and 2 illustrate a retractor illumination system implemented by modification of a typical retractor. In FIG. 1, retractor 3 is fitted with a light guide insert 5 which is mounted on the retractor, such that a light emitting surface 7 of the light guide faces the open surgical field 9. The light guide insert 5 may be mounted on the field surface of the retractor, or it may be mounted on the back side of the retractor, so long as a light emitting portion 7 of light guide 5 is exposed to illuminate surgical field 9, for example, through a cut out formed in the retractor or from around one or more sides of the retractor. Light guide insert 5 of FIG. 1 may be formed of any suitable material such as transparent or translucent material, shaped to conform to the surface of retractor 3 and includes one or more mating structures for releasable or fixed attachment to the retractor. A light source 11 may be mounted on the distal end of the retractor, in optical communication with the light guide, and may be a small self contained LED light engine mounted on the handle portion of the retractor, as shown, or a fiber optic cable carrying light from a remote laser or other suitable light source.

Figure 3:
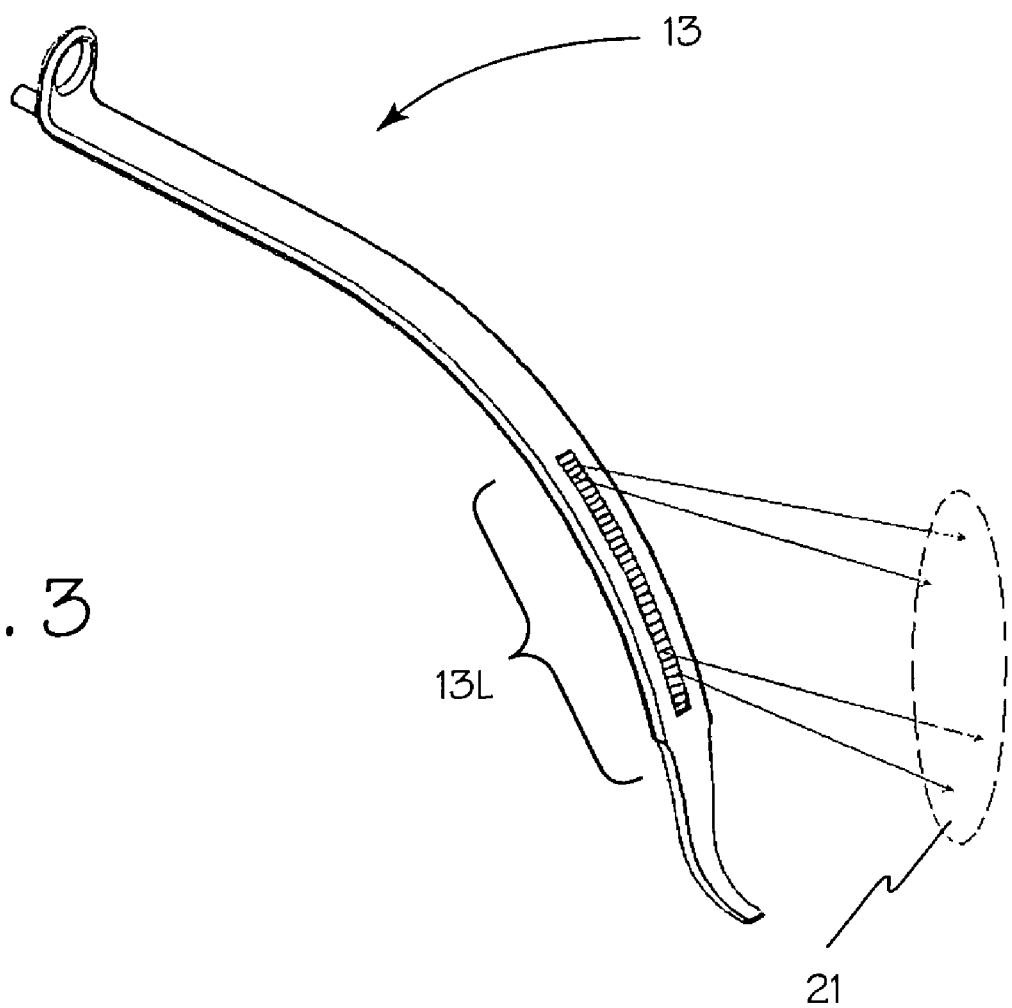
FIG. 3 is the integrated illuminating retractor of FIG. 2 with an alternatively configured light guide.

In FIG. 2, integrated illuminating retractor 13 is fabricated from a suitable light guide material, and a light source is operably connected to an input aperture 15 provided on the proximal handle portion of the retractor. The light guide, whether distinct from the retractor or integrally formed as a retractor, is modified at various portions along its length to emit and direct light to a nominal illumination field, such as surgical field 17 which is near the distal blade portion of retractor 13 when in use. The nominal illumination field is based on the particular retractor type and general surgical procedure in which the retractor will be used. In an operation such as total hip arthroplasty, during broaching for example, the surgical field will include the femoral neck, and the surgical field will be as illustrated in FIG. 1, above the hook 19 of the retractor and below the light emitting section, and on a plane substantially perpendicular to the long axis of the lower portion of the retractor. In other surgeries, it may be required to direct light to a plane substantially below the tip of the retractor (for example, surgical field 17 as shown in FIG. 2) or substantially parallel to lower portion 13L of retractor 13 (for example, surgical field 21 as shown in FIG. 3).

FIGS. 4 and 5 show a light guide 23 for use as a light guide insert (as in FIG. 1) or, if made of rigid and tough material such as a polycarbonate, as a simple hook retractor or blade retractor. The light guide proximal end 23P includes a light receiving aperture 25 which is adapted to be optically coupled to a light engine or a fiber optic bundle fed by a higher power light source. A portion of the blade, on the front surface 23F of the blade, may be faceted with one or more facets such as facets 27, which permit light passing through the light guide to be directed onto a surgical field. Each facet may be considered to be in the form of a stair step with a riser surface such as surface 27R and a step surface such as surface 27S.

In this embodiment, the step surface generally supports total internal reflection whereas the riser surface is typically the light emitting surface. Refraction of the light at the riser surface of the facet (typically air is the other medium) results in significant change of direction of the light emerging from each facet, so the facets are angled, relative to the axis of the device and the surgical field, to refract light toward the surgical field. The angle between the step surface and the riser surface may be chosen to maximize light directing and light extracting functions for each facet, and this angle may be different from facet to facet. While the riser and step surfaces are typically flat, they may also have more complex shapes to control light within the light guide or to direct light out of the light guide. For example, the riser surface may include microstructures to shape the light exiting that surface. Laterally, each riser may be straight or may have some other shape, such as convex or concave. The spacing of the stepped facets along the light guide may be described by a mathematical formula and or may be irregular or aperiodic. The size of the facets may be regular or irregular along the light guide. In addition, the step surface may be coated, for example, with a metallic reflective coating, to promote total internal reflection.

By providing numerous facets, the surgical field may be illuminated with numerous rays and may appear to be uniformly illuminated. Fewer facets may be used but may result in some areas receiving more illumination than other areas, which may or may not be desirable. A single facet may be used, for example, by cutting off the end of the light guide, but this approach lacks the light directing capabilities of the configurations described herein. Light directing capabilities of such a single facet may be improved by shaping the facet, for example, angling the face or providing a concave or convex face, and or by adding micro-structures to shape the profile of the light beam.

The back side of the light blade, lower surface 23L, near the distal tip 23D, may include angled facets 29 to cause internal reflections of light rays remaining in the light guide, reflecting those rays toward the surgical field at an angle to the front surface (at the distal tip) sufficient to permit passage of those light rays past the surface of the light guide (without all being reflected back into the light guide). The light guide front surface at the distal tip may have additional light directing structures, such as a molded or foil-stamped micro-structure diffuser or diffusing film. Again, numerous facets are provided, and the angles of the reflecting surface of the back facets are selected, relative to the incoming light and the surgical field, to create a uniform illumination. FIG. 6 provides a side view of light guide 23, illustrating the placement of the facets 27 and 29 and rough angles of the diffracting and reflecting faces of the facets.

The faceted area may vary, depending on the application. For the retractors illustrated, faceted areas of about 10 to 30 mm long, and 10 to 30 mm wide, are provided. This provides good illumination for many typical surgeries. One or more facets may be placed at different zones along the light guide to illuminate different parts of the surgical field, and the facets in each of these zones may have different design characteristics to meet illumination needs. For example, it may be desirable to have one part of a surgical field illuminated with a focused beam to create a bright spot whereas another part of the surgical field may require a more diffuse illumination. Alternatively, it may be desirable to have the light directed to the side so that the retractor may be placed in one area but illuminate a nearby area that is off to the side of the retractor. Though shown in very large scale in the drawing, the preferred size of the facets is about 25 to 500 microns, more preferably about 50 microns, which will provide illumination without perceptible dark and light bands on the surgical field. The facets may be curved, as shown, in the manner of Fresnel facets (though the function is to redirect light rays parallel to the plane of the light guide) to focus the escaping light onto a particlular area or more narrowly defined nominal surgical field. Each facet distal face is angled differently, depending on its position on the light guide and the desired illumination field. The actual angles to be used are dependant on the particular retractor, the particular light guide material, the light guide geometry, and the geometry of the desired illumination zone.

Placement and design of facets and the features that support total internal reflection may need to be altered for a substantially flat light guide versus a substantially curved light guide or a light guide with both flat and curved geometries. Facets may be provided only on the front face or only on the rear face, or both depending on the illumination needs. The combination of light control features described herein improves the overall efficiency of the light guide by ensuring that most of the light in the light guide is directed toward the surgical field. For example, we have found that the light guide of FIG. 4, when fabricated from silicone, has greater than 65 percent efficiency as compared to less than 40 percent efficiency for optical fiber based devices. In addition, other features are normally included as part of efficient light guide design, such as a surface roughness less than 500 Angstroms in variation, preferably less than 100 Angstroms, in order to maximize total internal reflection and minimize light loss in the light guide itself, both of which contribute to overall efficiency. Lower absorption materials and/or coatings, such as reflective coatings or films, are also preferred to maximize efficiency. Additional design elements may be included in the light guide to maximize efficiency, that is, to maximize the ratio of the amount of light illuminating the target area to the amount of light entering the light guide at its input. It is preferred that the light emitting structures be designed to minimize light directed back up into the surgeon's eyes to minimize eye fatigue and perceived glare.

The dimensions of light guide 23 in FIG. 4 change along its length. The thickness T decreases from input 25 (proximal) to the opposite tip (distal). The stepped facets serve to remove material, making light guide 23 thinner toward the distal end 23D to minimize its impact on the surgical work space and not hinder the surgeon's ability to manipulate instruments within that space. Light guide 23 gets wider along dimension W from the proximal to distal ends. This improves the ability to generate a wider beam. In another embodiment the light guide may be made to taper distally, in excess of any material reduction that may be caused by light directing structures. This causes the numerical aperture to increase as the area decreases. The angle of some of the light thus increases, which can be used to advantage to create a wider beam. Thus, the cross-section of a light guide may be changed from proximal to distal ends to improve light directing capabilities.

The invention is illustrated with a flat blade retractor, but it may be implemented in various forms including Steinman pins, cylindrical spinal retractors, hooks, converse blade retractors, right angle retractors, Desmarres lid retractors, lumbar retractor blades, laryngoscope blades, malleable retractors (provided the light guide is malleable or flexible), dental retractors and various other retractors. The facets may be formed as ridges, steps, or distally facing shoulders cut into or built up upon the face of the light guide.

Figure 7:
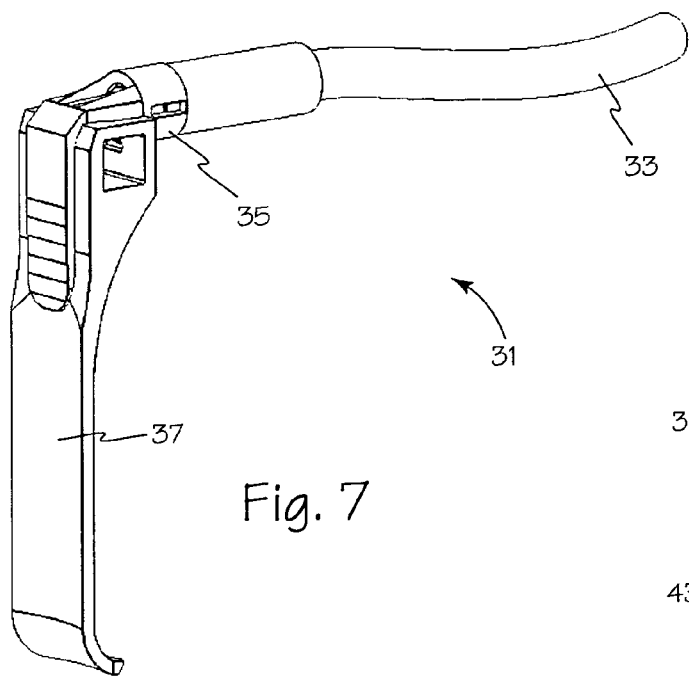
FIG. 7 is a light guide releasably attached to a right angle retractor blade with a fiber optic cable attached to the light guide.

FIG. 7 shows a retractor blade illuminator 31 with fiber optic cable 33 shown connected to light guide 35 that is releasably attached to right angle blade retractor 37. Any suitable right angle blade retractor may be used such as McCulloch, Caspar, Taylor, Meyeding or any other. In this illustration a narrow McCulloch style retractor is shown. Light guide 35 may be scaled to any size of blade retractor. In this particular embodiment, the fiber optic cable has a male connector and the light guide has a corresponding female connector, but the opposite arrangement may also be used. Coupling of light from the fiber optic cable to the light guide is typically through a simple face-to-face coupling, typically with a small air gap between the two faces. The coupling interface may also be accomplished with an index matching material to facilitate light transfer. In some applications, it may be desirable to include other elements in the coupling interface such as focusing lenses or protective sapphire windows.

Figure 8:
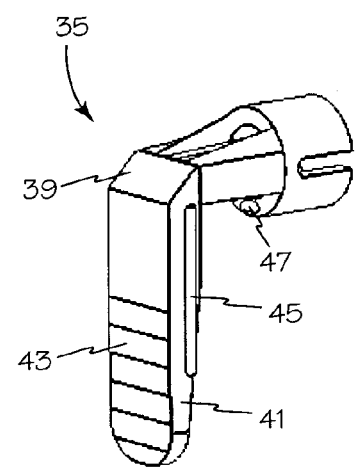
FIG. 8 is a perspective view of the light guide of FIG. 7.
Figure 9:
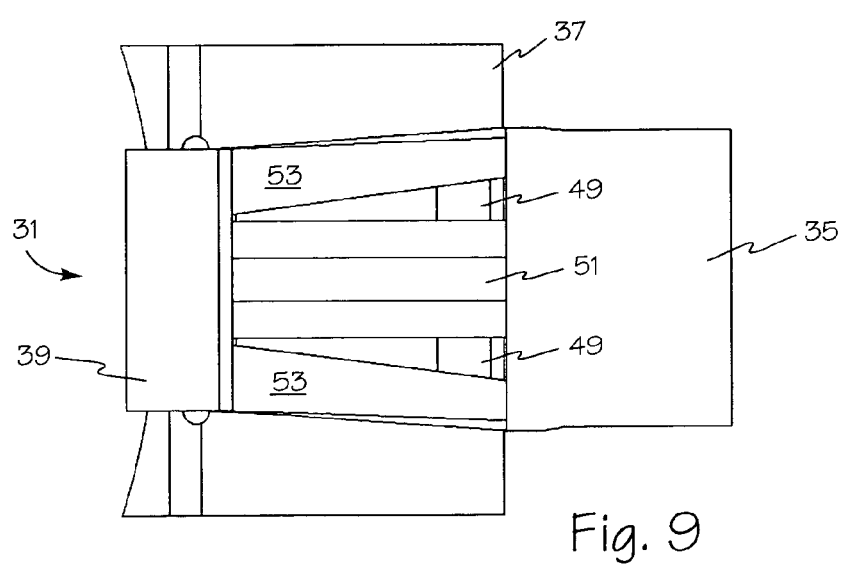
FIG. 9 is a top view of the light guide and right angle blade retractor of FIG. 7.

FIG. 8 shows light guide 35 with primary light directing structure 39 that directs incoming light orthogonally to light directing structures 41 on the rear face and light directing structures 43 on the front face. Rear light directing structure 41 may be a simple ramp surface, a series of angled or stepped surfaces as shown in FIG. 5, or other suitable light directing structures. Also shown is slide engagement structure 45 that engages a corresponding slide structure in the retractor, as well as snap feature 47 that helps hold the light guide in place on the retractor. FIG. 9 shows a top view of retractor blade illuminator 31 with light guide 35 on retractor 37 with primary light directing structure 39. An important element of this embodiment is the inclusion of air gap 49 around light conducting structure 51 that separates light conducting structure 51 from structural members 53. All light conducting structures should minimize any contact with supporting structures in order to reduce the light loss that would occur either through internal reflection or through refraction at the interface of two different materials with different indices of refraction. Careful consideration of the light conducting pathway and use of air gaps at supporting structures, which may be integral to the light guide or may be made from other materials and attached to the light guide, help minimize light loss. For this and other embodiments, the thickness and width tapering techniques described in relation to FIG. 4 may be applied.

Figure 10:
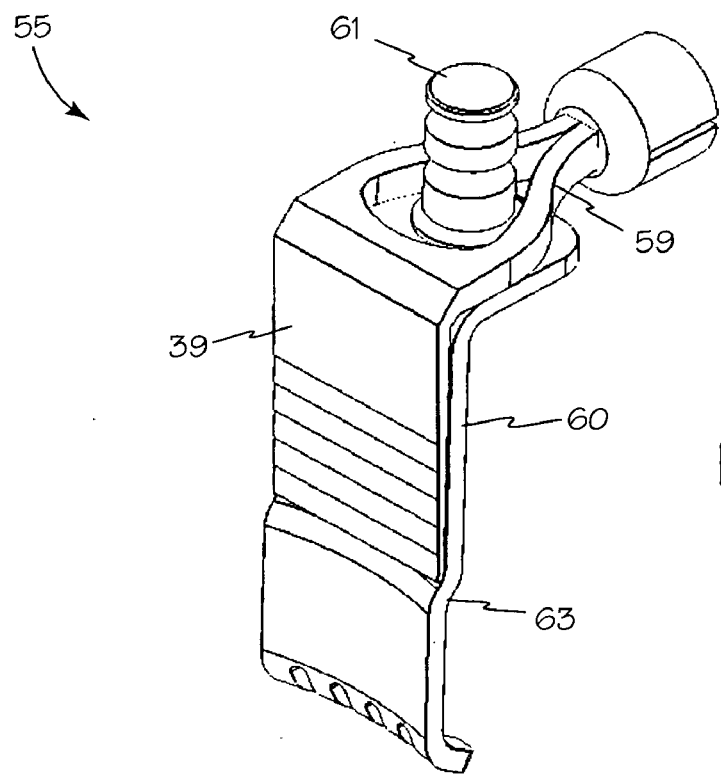
FIG. 10 is a light guide modified to fit a Caspar style blade retractor.

FIG. 10 shows an alternative embodiment for a Caspar style blade retractor illuminator system 55. Light guide 57 includes split light conductor 59 that goes around head 61 to which holders and other instruments are attached to hold or manipulate the retractor. The blade body 60 has bend 63 which provides an extension of the front surface of the light guide to mimic the vertically flat surface of a standard Caspar style blade retractor and so that the light guide does not extend into the surgical field created by the retractor. Without bend 63, the bottom of the light guide would be fully exposed, thereby allowing other light directing structures to be positioned at the bottom surface, for example, to shine light straight down the face of the retractor blade.

Figure 11:
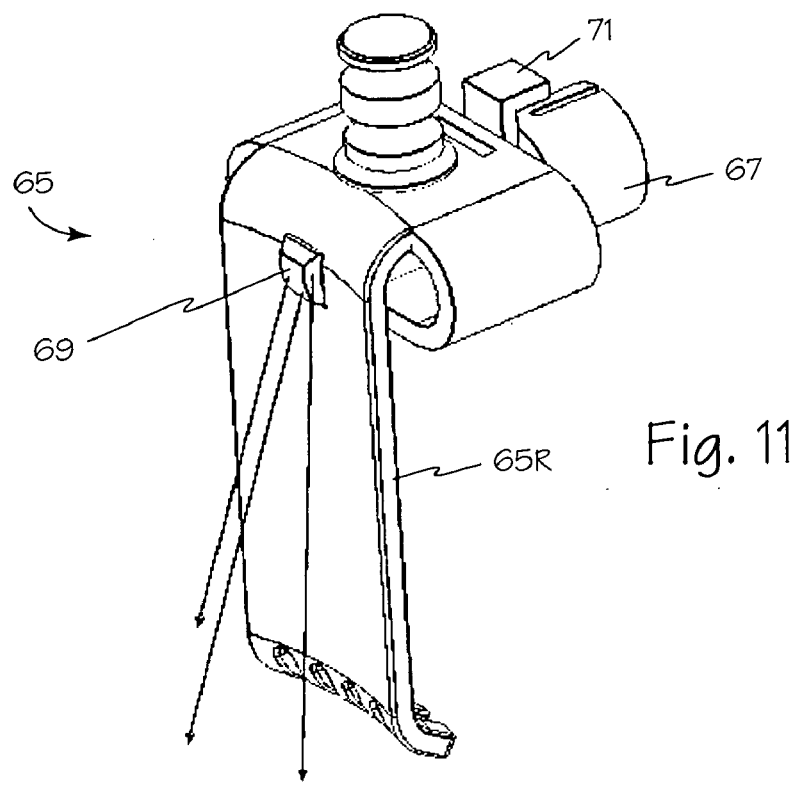
FIG. 11 is a light guide that snaps into the rear of a modified Caspar style blade retractor with light directing structures exposed through a cutout in the blade face.

In FIG. 11 illuminating retractor 65 includes Caspar style blade retractor 65R and light guide 67 engaging the rear of the retractor. Light emitting portion 69 is designed to project light down as illustrated. Spring snap 71 engages light guide 67 into the area formed by bends in the light guide as illustrated. While light emitter 69 works well, it may cast undesired shadows on to the surgical field when instruments are used. As such, a longer light emitting section, such as that shown in FIG. 4 or FIG. 8 but still coming through from the back side, may be preferred to reduce shadowing. In addition, the light emitting surface area is preferably made as large as possible to reduce the effects of splattered blood or tissue, which will occlude areas of the light emitting area leaving unsplattered areas free to continue to provide illumination. The light guide of FIG. 8 may be adapted to fit into the retractor from behind, exposing the light emitting surface through a cutout in the retractor so that light can illuminate the surgical field.

Figure 12:
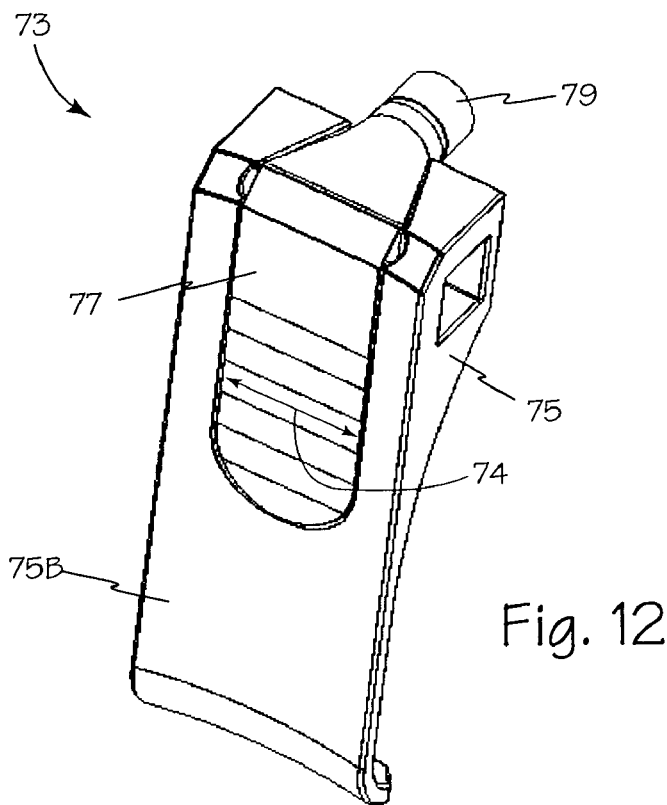
FIG. 12 is a light guide designed for a wide style McCulloch blade retractor.

FIG. 12 shows an alternative embodiment for a McCulloch style illumination retractor system 73. Retractor 75 is similar to FIG. 7 except that blade 75B is a wide style requiring light guide 77 to be made wider along dimension 74. While the narrow light guide of FIG. 7 can be made to fit the wide style blade, the narrowness of the light guide may restrict options for directing light in a wide enough illumination zone for the types of surgeries in which the wide style blade is used. A wider light guide generally provides more options for illuminating a wider illumination zone. The light guide may be narrow at the top portion and wider at the lower portion, or visa versa, to provide options for illuminating both narrow and wide illumination zones. In addition, light input connector 79 is male.

Figure 13:
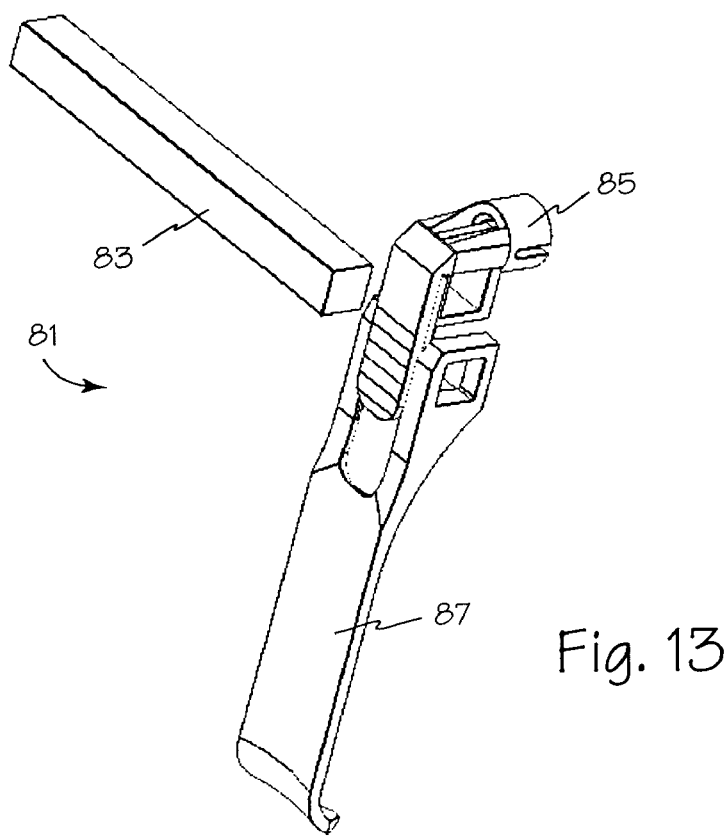
FIG. 13 is an alternative configuration for securing the light guide to the blade retractor using the frame support arm normally attached to the blade retractor.

FIG. 13 shows illuminating retractor system 81 with an alternative light guide holding method relative to FIG. 7 in which frame support arm 83 is used to lock in light guide 85 when it is engaged into retractor 87.

Figure 14:
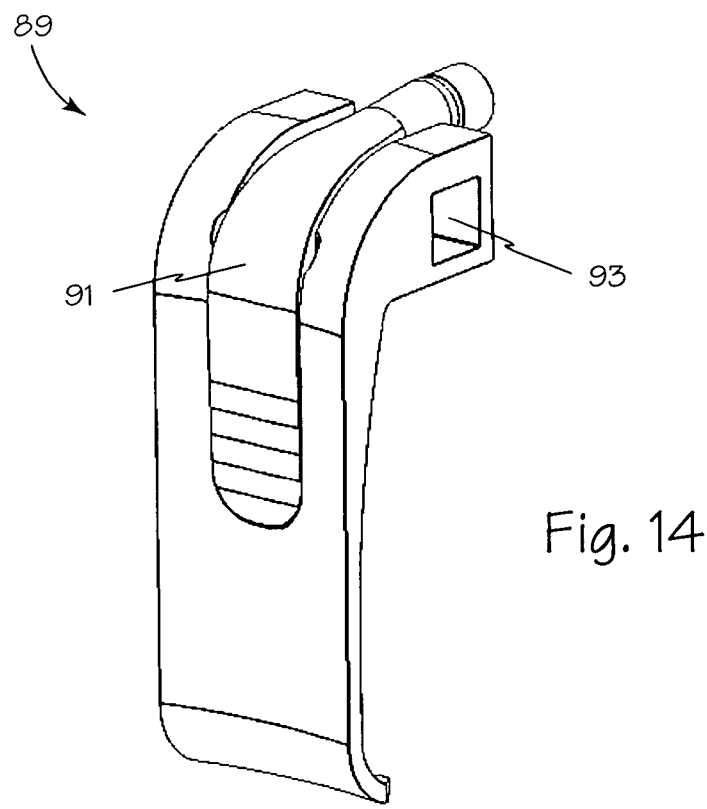
FIG. 14 is a light guide adapted to engage an offset style McCulloch blade retractor.

FIG. 14 shows illuminating retractor system 89, which is an alternative embodiment to FIG. 12, in which the primary orthogonal light directing structure 39 is replaced by a gradual radius 91 on the front edge. This allows hole 93 for the support frame bar to be moved back, creating an offset style retractor blade as is known in the art. Radius 91 provides substantially more work room for instruments than the more squared-off edge shown in FIG. 12.

Figure 15:
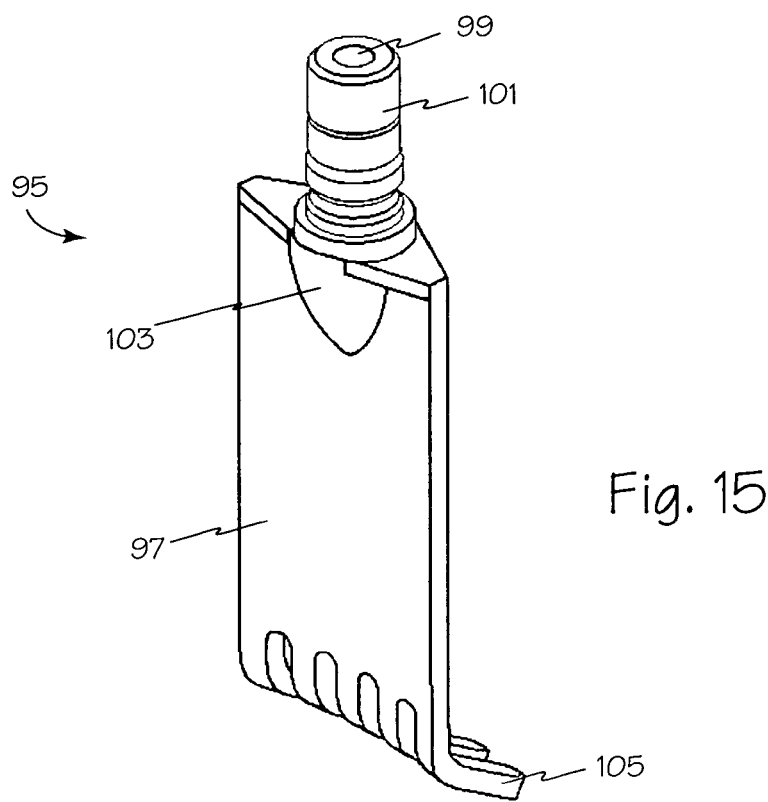
FIG. 15 is an integrated illuminating blade retractor in the Caspar style.

FIG. 15 illustrates a Caspar style blade retractor 95 wherein body 97 is formed entirely from light guide material, with a cylindrical light input portion 99 extending to the tip of head 101. Head 101 is preferably made from metal and may be attached or insert molded. Optical element 103 may be a structure for directing light, such as a compound parabolic concentrator, serving to collect light from the input portion 99 and directing that light into body 97. Light directing structures, sometimes also referred to as light extraction structures, may be placed on the outer and or inner face of body 97 and or along the tangs 105 to send light directly under the tangs into an area of the surgical field sometimes referred to as the "gutter" which is sometimes necessary to see.

Figure 16:
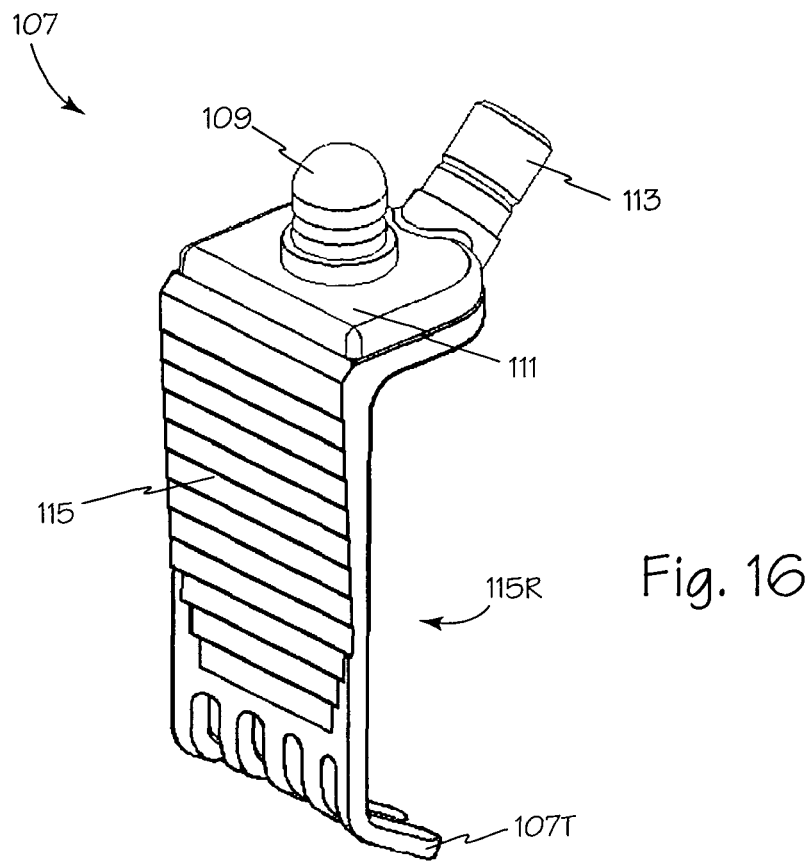
FIG. 16 is an alternative configuration of the Caspar style integrated illuminating blade retractor.

In this configuration, head portion 101 is directly adjacent to the surgical work area, so any attachments such as holders or manipulators may get in the way. FIG. 16 shows a preferred Caspar style illuminating retractor 107 that more closely mimics a full metal Caspar retractor. Head portion 109 is positioned on base 111, both of which may be plastic or metal. Head 109 may be integral with base 111 or may be a separately attached component. Fiber Connector 113, for example, may be an industry standard ACMI or Wolf connector or a proprietary connector used to connect to a source of light, is preferably an integral part of base 111, but may be a separate component. Light guide body 115 includes light extraction facets on its front face and may have addition light extraction structures on the lower tangs 107T. Rear surface 115R of body 115 may be radiused to provide strength and light direction, that is, a light directing structure may also perform another function, such as adding mechanical strength. Other light directing or light extracting structures may be placed on other surfaces of body 115 as needed to provide specific illumination to specific areas of the surgical field. In addition, a film laminate of known index of refraction may be placed on rear surface, which is placed directly on body tissues of varying refractive indices that may contribute to light loss. Such a film may perform another function by holding together parts of a plastic retractor that fractures or breaks during tissue retraction.

Figure 17:
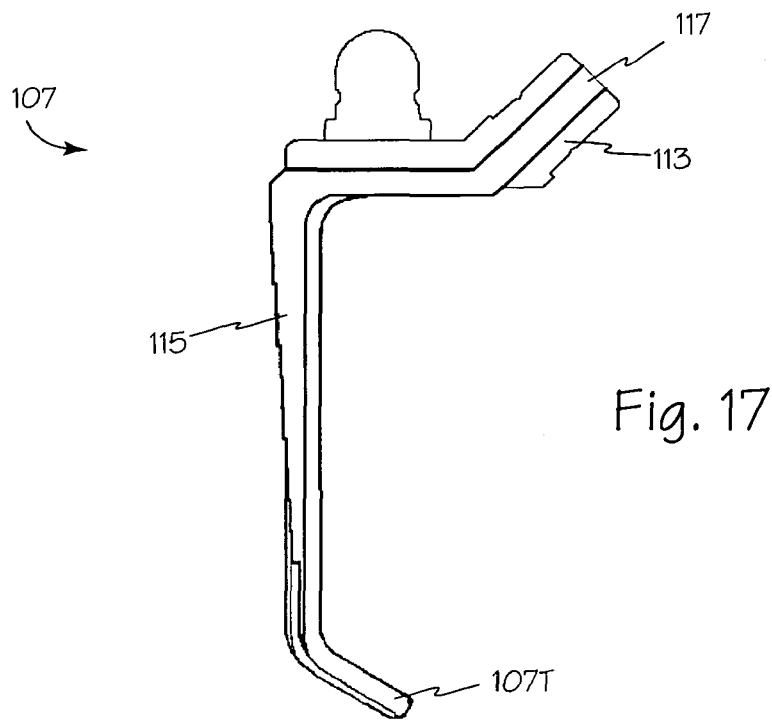
FIG. 17 is a section view of the integrated illuminating retractor of FIG. 16.

FIG. 17 is a side view section of illuminating retractor 107 in FIG. 16 showing that light guide body 115 is continuous with light input portion 117 in connector 113. Light input portion 117 may include light capturing and or directing structures that can be hidden in connector 113, such a taper or compound parabolic concentrator. Air gaps may occur between the light input face and the light source. Since light immediately diverges as it exits the light source, some light may be lost around the input face. For example, a 3.5 mm diameter optical fiber device connected to a 4.0 mm diameter fiber optic cable would have lower efficiency due to the mismatch in diameters and divergent light loss across an air gap, e.g., a 0.5 mm air gap typical in ACMI connector systems.

Another aspect of an illuminating retractor is for the input face of the input connector to be larger than the mating light source to gather the divergent light into the light guide. For example, simple geometry shows that a 5.6 mm diameter light guide input will gather divergent light from a 4.0 mm fiber bundle with a 0.5 mm gap between the two and assuming a numerical aperture of 0.55 in the light source. If size is restricted, use of alternate input geometries still improves efficiency. For example, a 4 mm square input captures some divergent light at its corners from a 4 mm diameter light source. Divergent light loss is a significant contributor to heat generation in metal connectors in fiber optic systems. These concepts will reduce this heat and thereby reduce the likelihood that a patient may receive a burn, which is a hazard associated with such systems. In addition to adjusting the size of the light guide input, the plastic light guide can incorporate a plastic female connector to a metal male connector on a typical fiber optic cable. Plastic will not conduct the heat as readily as a metal female connector. Focusing lenses can also be used, but these add cost to any assembly.

Figure 18:
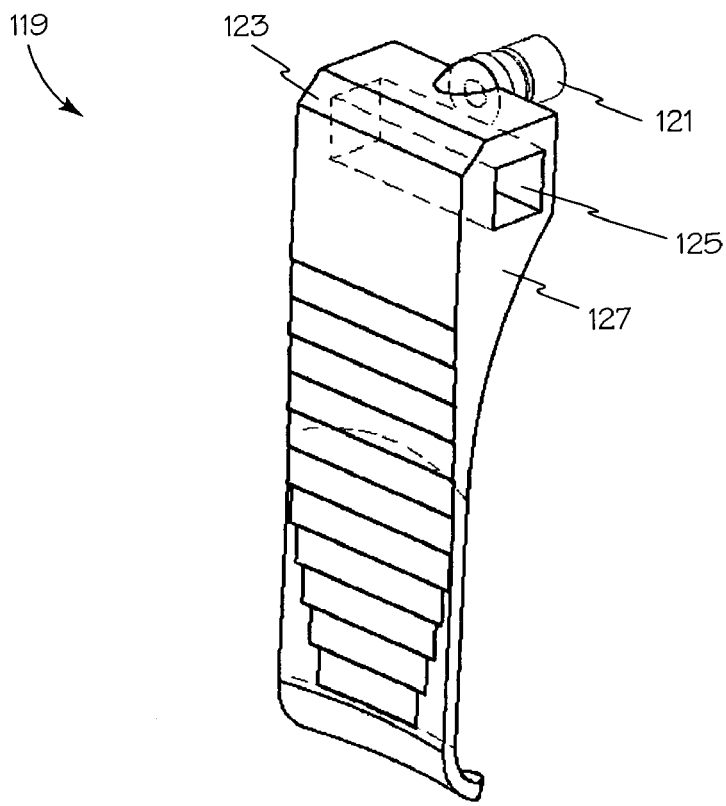
FIG. 18 is an integrated illuminating blade retractor in the McCulloch style.
Figure 19:
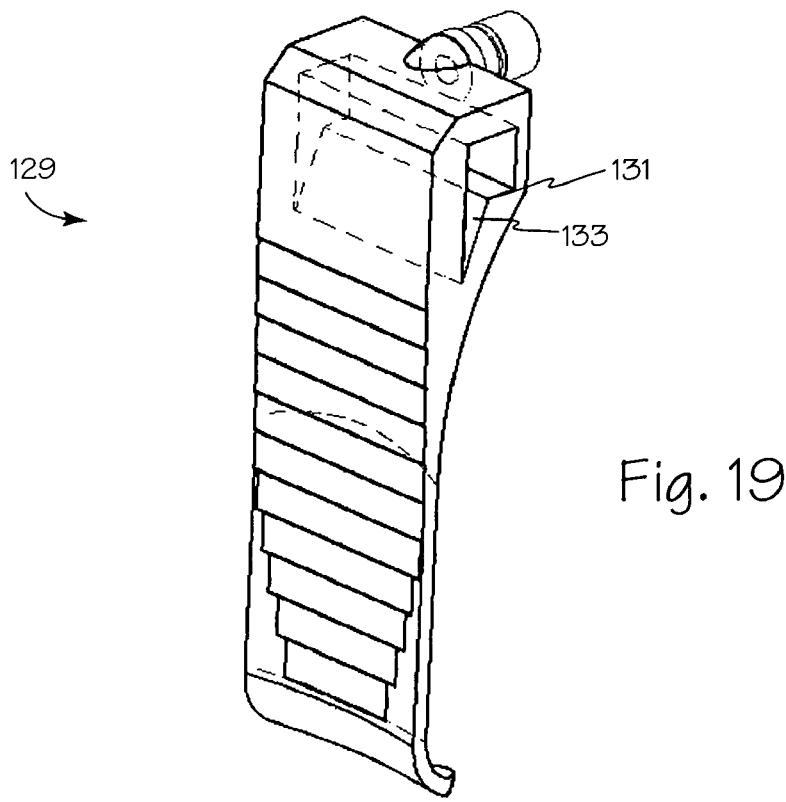
FIG. 19 is an adaptation of the integrated illuminating retractor of FIG. 18.

FIG. 18 shows a McCulloch blade retractor fashioned as a fully integrated light guide 119. Light enters connector 121, then hits orthogonally directing reflector 123. Some light may be reflected off of the front wall of channel 125. Some light may enter the back area 127 and may become lost due to internal reflections that may not direct the light in a downward direction. The alternative integrated illuminating retractor 129 of FIG. 19 solves this problem by providing air gap 131 that creates longer reflecting wall 133, which serves to directly light better in the downward direction. This, an optical path in a light guide may be protected from mechanical features in the same light guide. The fully integrated light guide may be strengthened by conversion to a composite structure in which structural elements are added to the light guide. Structural elements may be added to the plastic light guide itself, such as fillets, gussets or ribs. Structural members, such as a metal or reinforced plastic I-beam, bar or tube, can be co-molded with the light guide. In this case, such structural members are preferably placed in areas where there is not much light in the light guide to avoid interference with the carefully designed light path within the light guide. Such structural members may include polished surfaces that may be included in the light path design, for example, as intentional reflectors. Metal or reinforced plastic backbones may be adhered to the light guide to add strength, but the placement and materials characteristics must be considered during light path design. The surfaces of some materials may be treated to add stiffness, but any such surface treatment must be considered for its effect on the light path design, for example, it may add a new layer with a different index of refraction than the untreated material. As noted above, a film may be added for certain optical properties (e.g., reflection or diffusion). Such films may add strength to the final assembly and help prevent release of fragments into the surgical field in case the part fractures.

Figure 20:
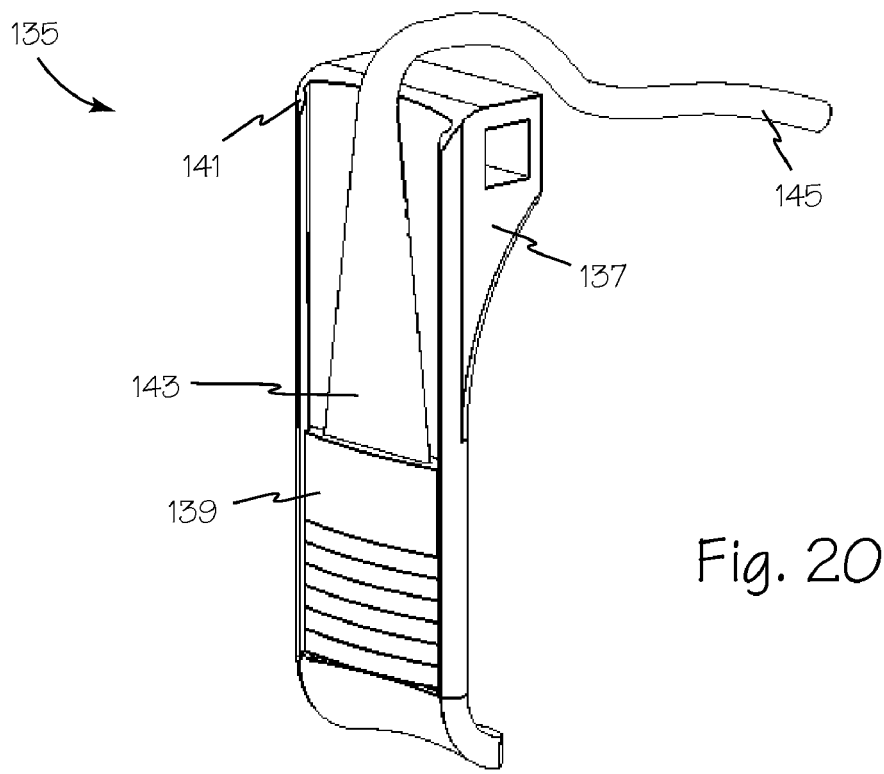
FIG. 20 is a light guide with a flexible input section.
Figure 21:
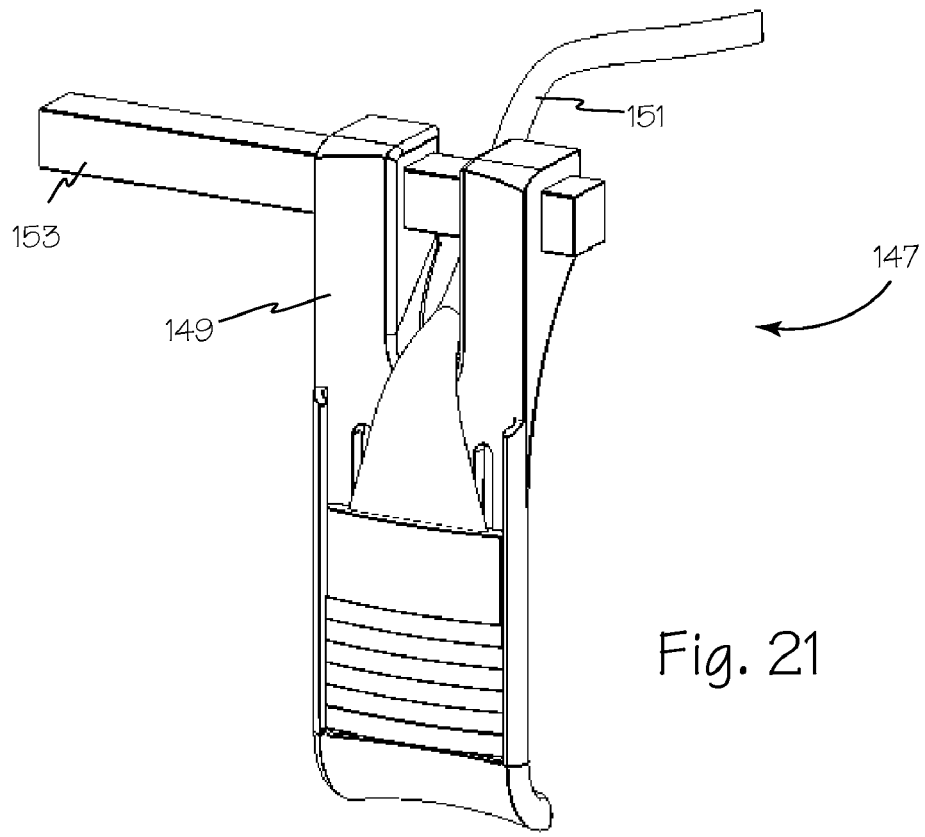
FIG. 21 is an alternate configuration of the light guide of FIG. 20.

FIG. 20 shows an alternative retractor illumination system 135 comprised of retractor 137 configured to allow light guide 139 to slide into grooves 141 formed into retractor 137. Alternatively, light guide 139 may be configured to slide around the sides of retractor 137 or snap onto or into retractor 137. Light guide 139 has flexible input 143 that is attached to light guide using a suitable method, such as insert molding, co-molding or via adhesive, preferably an index matching adhesive to minimize light loss at it transfers from flexible input 143 into light guide 139. Flexible input 143 may be formed from a suitable, flexible, light conducting material such as a fiber optic cable or silicone. Flexible input 143 may be flared into light guide 139 to help start distributing light across the width of light guide 139 and to match the thin profile of light guide 139 inside of the surgical work space. Proximal end 145 of flexible input 143 may be a short length of flexible material with a suitable optical connector to create a "pigtail" that is connected via a separate fiber optic cable to a light source, or it may be of a longer length to form a cable that connects directly to a suitable light source. This embodiment suffers in that flexible input 143 lies over the top of retractor 137 and may be subject to damage from instruments used during surgery. Alternative retractor illumination system 147 shown in FIG. 21 addresses this issue by modifying retractor 149 to allow flexible input 151 to be position underneath frame bar 153 and thereby protecting flexible input 151.

Multiple blade retractor illuminators of the types described herein may be used in a particular surgery in order to provide for different illumination needs. For example, an illuminator designed to provide a more high intensity spot of light may be used with an illuminator designed to provide a more diffuse, wider angle light beam. In addition, different frequencies of light may be used to improve visualization of specific tissues and or polarization elements may be integrated in the light guide to reduce glare. The light guides can also include other functions, such as providing separate channels for ventilation, irrigation and or suction using the concept of air gaps or insert molded metal reflectors to separate the optical path from these other functions within the same light guide.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A medical retractor illumination system comprising:
a retractor having a front surface facing a surgical field, a rear surface, a distal and a proximal end and a shape, wherein the rear surface is adapted to engage tissue to expose the surgical field;
a light guide disposed over the front surface and conforming to the shape of the retractor and removably secured to the retractor to conduct light through the front and rear surfaces of the retractor, the light guide having an input adapter and one or more light emitting surfaces comprising a plurality of facets, and wherein the light guide has a cross-section with a width and thickness, the thickness changing from a proximal end of the light guide toward a distal end thereof, and
wherein the light guide comprises a plurality of zones for illuminating the surgical field, the plurality of facets disposed in the plurality of zones, and wherein at least some of the plurality of facets in a first zone are different than the plurality of facets in a second zone; and
a light source providing illumination energy to the input adapter.

2. The medical retractor illumination system of claim 1 wherein at least one of the light emitting surfaces comprises a plurality of steps.

3. The medical retractor illumination system of claim 1 wherein at least one of the light emitting surfaces comprises a plurality of curved facets.

4. The medical retractor illumination system of claim 1 wherein the retractor is a McCulloch blade retractor.

5. The medical retractor illumination system of claim 1 wherein the retractor is a Caspar blade retractor.

6. The medical retractor illumination system of claim 1 wherein the retractor is an offset McCulloch blade retractor.

7. The medical retractor illumination system of claim 1 wherein the width of the light guide changes from the proximal end of the light guide to the distal end thereof.

8. The medical retractor illumination system of claim 1 wherein the input adapter comprises a round cross-section transitioning into a rectangular cross-section.

9. A surgical illumination system comprising:
a retractor having a proximal handle portion and a distal portion adapted for insertion into a surgical field and retraction of body tissue, and wherein the retractor has a front surface facing the surgical field and a rear surface adapted to engage tissue to expose the surgical field;
a light guide disposed over the front surface of the retractor, said light guide having a distal surface adapted to face the surgical field when in use in retracting body tissue away from a surgical field, and wherein the light guide has a cross-section with a width and thickness, the thickness changing from a proximal end of the light guide toward a distal end thereof; and
a proximal aperture adapted to receive light from a light engine or other light source;
wherein a portion of the distal surface of the light guide is faceted with a plurality of facets, ridges, steps or shoulders, wherein a distally oriented surface of said plurality of facets, ridges, steps or shoulders are angled relative to the axis of the light guide and the location of the surgical field such that light passing through the light guide is emitted and directed toward the surgical field, and
wherein the light guide comprises a plurality of zones for illuminating the surgical field, the plurality of facets disposed in the plurality of zones, and wherein at least some of the plurality of facets in a first zone are different than the plurality of facets in a second zone.

10. The illumination system of claim 9 wherein a portion of the distal surface of the light guide opposite the surgical field is faceted with a plurality of facets, ridges, steps or shoulders, where a distally oriented surface of said plurality of facets, ridges, steps or shoulders are angled relative to the axis of the light guide and the location of the surgical field such that light passing through the light guide is reflected from the plurality of facets, ridges, steps or shoulders toward the surgical field then emitted and directed toward the surgical field.

11. The illumination system of claim 9 wherein the width of the light guide changes from the proximal end of the light guide to the distal end thereof.

12. The illumination system of claim 9 further comprising an input adapter coupled to the proximal aperture and adapted to deliver light from a light source to the light guide, wherein the input adapter comprises a round cross-section transitioning into a rectangular cross-section.

* * * * *